United States Patent [19]

Hidaka et al.

[11] Patent Number: 4,943,581
[45] Date of Patent: Jul. 24, 1990

[54] ISOQUINOLINESULFONAMIDES

[75] Inventors: Hiroyoshi Hidaka, 799-75 Kannonjicho; Toshio Tanaka, both of Tsushi; Yasuo Itoh, Katsuyamashi; Hideo Kato, Fukuishi; Eiichi Koshinaka, Katsuyamashi; Kazuya Mitani, Fukuishi; Shunichiro Sakurai, Katsuyamashi, all of Japan

[73] Assignees: Hokuriku Pharmaceutical Co., Ltd., Katsuyamashi; Hiroyoshi Hidaka, Tsushi Mie, both of Japan

[21] Appl. No.: 371,392

[22] Filed: Jun. 26, 1989

[30] Foreign Application Priority Data

Jul. 4, 1988 [JP] Japan .................... 63-165050

[51] Int. Cl.$^5$ .................... A61K 31/47; C07D 217/22
[52] U.S. Cl. .................... 514/307; 546/139
[58] Field of Search .................... 546/139; 514/307

[56] References Cited

U.S. PATENT DOCUMENTS 4,525,589 6/1985 Hidaka et al. .................... 546/139
4,709,032 11/1987 Hidaka et al. .................... 546/139

Primary Examiner—Richard L. Raymond
Assistant Examiner—James H. Turnipseed
Attorney, Agent, or Firm—Gordon W. Hueschen

[57] ABSTRACT

An isoquinolinesulfonamide selected from those represented by the formula:

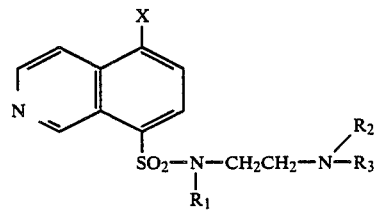

wherein $R_1$, $R_2$ and $R_3$ may be the same or different, and each represent hydrogen or lower-alkyl, and X represents hydrogen or halogen, and pharmacologically-acceptable acid addition salts thereof, pharmaceutical compositions thereof, and use thereof in the treatment of circular disorders, are disclosed.

4 Claims, No Drawings

ISOQUINOLINESULFONAMIDES

BACKGROUND OF THE INVENTION

The present invention relates to a novel isoquinolinesulfonamide* or its pharmacologically-acceptable acid addition salts which are useful as agents for treating ailments of the circulatory system and as biochemical tools. * which is not described in the literatures.

Known compounds used as vasodilators, hypotensives, agents for improving cerebral circulation, agents for treating stenocardia, and agents for prevention and treatment of thrombosis of cerebral and cardiac blood vessels, should be improved upon, for example, from the standpoint of improving effectiveness, selectivity on circulatory organs, and of safety.

After investigation of numerous compounds useful as vasodilators, hypotensives, agents for improving cerebral circulation, agents for treating stenocardia, and for prevention and treatment of thrombosis of cerebral and cardiac blood vessels, it has been found that the novel isoquinolinesulfonamides of the present invention have excellent properties in the field of interest.

DETAILED DESCRIPTION OF THE INVENTION

The present invention provides isoquinolinesulfonamides represented by the following formula (I):

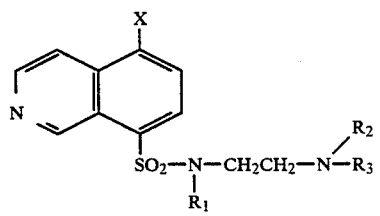

wherein $R_1$, $R_2$ and $R_3$ may be the same or different, and each represent hydrogen or lower-alkyl, and X represents hydrogen or halogen, or pharmacologically-acceptable acid addition salts thereof.

In this invention, examples of lower-alkyl represented by $R_1$, $R_2$ and $R_3$ in the formula (I) are methyl, ethyl, n-propyl, isopropyl, n-butyl, isobutyl, sec-butyl, tert-butyl, and the like and halogen represented by X are fluorine, chlorine, or bromine.

The pharmacologically-acceptable acid addition salts of the compounds represented by the formula (I) of the present invention include, for example, mineral salts, such as the hydrochloride, hydrobromide, hydroiodide, nitrate, sulfate, phosphate and the like, and organic acid salts such as the acetate, maleate, fumarate, citrate, oxalate, tartarate, methanesulfonate, and the like.

The novel isoquinolinesulfonamides represented by the formula (I) can be prepared by various processes.

According to the first process, the compounds represented by the formula (I) can be prepared by the following scheme:

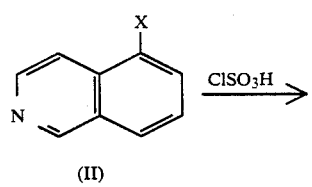

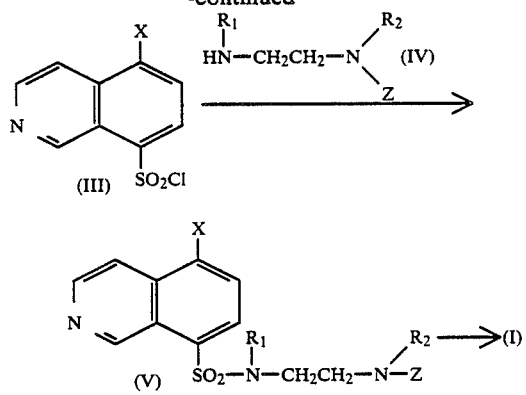

wherein $R_1$, $R_2$ and X have the same meanings as described above and Z means lower-alkyl or benzyloxycarbonyl.

Thus the isoquinoline represented by the formula (II) is reacted with chlorosulfonic acid with heating in the presence or absence of solvent and the thus-obtained sulfonyl compound represented by the formula (III) is reacted with the amine (IV) which is substituted by lower-alkyl or protected by benzyloxycarbonyl in an organic solvent. The thus-obtained compound represented by the formula (V) is, if necessary, treated with an acid or by means of catalytic reduction to remove the protective group to yield the desired compound having formula (I).

As solvent for reaction of the isoquinoline (II) with the chlorosulfonic acid, any solvent which is non-reactive with the reactants and reaction products can be used, for example, chloroform, methylene chloride, ethyl acetate, acetonitrile, dioxane, benzene, toluene, or the like. As solvent for reaction of the sulfonyl compound (III) with the amine (IV), any solvent which is non-reactive with the reactants and reaction products can be used, for example, chloroform, methylene chloride, ethyl acetate, acetonitrile, dioxane, N,N-dimethylformamide, benzene, toluene, methanol or the like. If necessary, a base such as triethylamine, pyridine, or the like can be added.

The reaction is carried out at a temperature within the range from 0° C. to the reflux temperature of the solvent used.

Examples of acids which can be used for removing the protective group are hydrochloric acid, hydrobromic acid, sulfuric acid, trifluoroacetic acid, and the like and examples of catalysts for catalytic reduction are palladium-carbon, platinum oxide, Raney nickel, and the like.

Examples of solvents for the reaction are water, methanol, ethanol, acetic acid, and the like.

The reaction is carried out at a temperature within the range from room temperature to the reflux temperature of the solvent used.

According to the second process, the compounds of this invention of the formula (I), wherein X means a hydrogen, can be prepared by catalytic reduction of the compound wherein X means a halogen, in the presence of a solvent.

As solvent for the reaction, any solve to which is non-reactive with the reactants and reaction products can be used, for example, methanol, ethanol, ethyl acetate, methanol containing ammonia, and the like.

Examples of catalysts for the catalytic reduction are palladium-carbon, platinum oxide, Raney nickel, and the like.

The reaction is carried out at a temperature within the range from 0° C. to the reflux temperature of the solvent used and at atmospheric pressure or under vacuum.

The isoquinolinesulfonamides of the present invention represented by the formula (I) have an inhibitory effect against carmodulin, as well as a strong depressive effect against the activity of myosin light-chain kinase. In consequence, these compounds effect relaxation of smooth muscle and vasodilation, so that they are useful as vasodilators, anti-hypertensives, drugs for improving cerebral circulation, agents for treating stenocardia, agents for the prevention and treatment of thrombosis in cerebral and cardiac blood vessels, and are also extremely useful as biochemical tools.

Compounds of the present invention represented by the formula (I) or a pharmacologically-acceptable acid addition salt thereof can be used as such, but are preferably administered together with any of the usual pharmaceutically- and preparatively-acceptable additives.

Representatively, the compounds of the present invention can be administrated per os, per mucosa, or by injection, for example in the form of pills or tablets, powders, granules, capsulated powders or granules, injection, suppositories, or the like. In oral and mucosal preparatious an excipient, a disintegrator, a binding agent, a glaze-agent, and/or a coating agent can be used as constituents whereas, for injection, a resolvent and resolvent adjuvant which can comprise water and/or a solvent, which can dissolve the components in use, a pH regulator, and/or a stabilizer can be employed.

The excipients used according to the present invention are, for example, lactose, starch, D-mannitol, crystal cellulose, calcium hydrogenphosphate, or dextrin. Exemplary disintegrators are carboxymethyl cellulose, calcium carboxymethyl cellulose, sodium closscarrmelose, and hydroxypropylstarch. Suitable binding agents are hydroxypropylcellulose, hydroxypropylmethyl cellulose, polyvinylpyrrolidone, methylcellulose, gum arabic powder, polyvinylalcohol, pluran, and gelatin. Representative glazing agents are magnesium stearate, talc, stearic acid, hardening oil, and light silicate anhydride. Representative coating agents are hydroxypropylmethyl cellulose, white sugar, ethyl cellulose, oidlagid L, polyethylene glycol, titanium oxide, and calcium sulfate. Suppository or other bases are polyethylene glycol, synthetic triglycerides, cacao butter, glycerol, and hard fat, and resolvents are distilled water for injection, isotonic sodium chloride solution, etc., whereas adjuvants for injection are propylene glycol, D-mannitol, etc., and pH regulators are inorganic acids such as hydrochloric acid or organic acids such as citric acid, tartaric acid, or a salt thereof.

The dosage regimen for the compounds of the present invention is usually 1–100 mg per day for an adult.

The effect on smooth muscles of blood vessels

A rabbit weighing 1.9–2.8 kg was bled to death, then the abdomen was opened, and the superior mesenteric artery (2.0–3.0 mm of outer diameter) was extracted. The extracted blood vessels were cut in the usual way into the form of spirals, and a specimen of 1.5–2.5 mm in width and 20–30 mm in length was formed. The spiral specimen was suspended in 20 ml organ bath comprising Krebs-Henseleit's solution, after which a tension of 2.0–0.5 g was loaded. The nutrient solution was warmed at 37°±0.5° C. and ventilated by mixed gas of 95% oxygen and 5% carbon dioxide. The lower end was fixed, whereas the upper end was attached to a force-displacement transducer (SB-1T) manufactured by Nihon Koden Company. The change of tension was recorded isometrically. The specimen was suspended for at least 60 minutes before the test was begun, and the nutrient solution was exchanged every 15 minutes to conduct the experiment in the meantime.

The relaxation effect upon the smooth muscle of the blood vessel was tested. Previously, the spiral specimen had been contracted with 20 mM of KCl and maintained at a certain tension; thereafter the test agent was added cumulatively. Contraction induced by 20 mM KCl was taken as 100% and the relaxation effect of the test agent was represented by $ED_{50}$ which was the concentration of the agent at which only 50% of the muscles remained shrunken.

Result is shown in Table 1.

TABLE 1

| Test compound | $ED_{50}$ ($\mu M$) |
|---|---|
| Example 1 | 32 |

The effects on myosin light-chain kinase

A myosin light chain of the smooth muscles of chicken gizzard was used as a substrate and the amount of radioactive phosphoric acid incorporated from [$\gamma$-32P] ATP into the substrate-protein was measured for a determination of the activity of the enzyme. The reaction solution, in an amount of 200 $\mu l$ as a whole, was constituted from 25 mM of Tris-HCl(pH 7.0), 10 mM $MgCl_2$, 40 $\mu g$ of myosin light chain (obtained by preparing myosin from the smooth muscle of chicken gizzard followed by guanidine denaturization), 200 $\mu M$ of $CaCl_2$, 80 ng of calmodulin (prepared from cattle brain), myosin light chain kinase (prepared from the smooth muscles of chicken gizzard), and agents of various concentrations. The reaction was started by the addition of 20 $\mu l$ of 100 $\mu M$ [$\gamma$-32P] ATP at 30 ° C., and stopped by the addition of 0.5 ml of 20% TCA. After the reaction was stopped, 3 ml of 5% TCA and 0.1 ml of 1 mg/ml albumin solution were added into the reaction mixture, the resulting solution was centrifuged, and the obtained acid-insoluble protein was fixed on the bottom of a test tube. Further, the supernatant was removed, 3 ml of 5% TCA was added into the residue, and the solution was centrifuged. The operation was repeated two or three times. The precipitated protein was dissolved with 2 ml of 1 N NaOH, transferred to a vial containing about 10 ml of water, and measured for Cherenkov effect by a liquid scintillation counter. The activity in the presence of calcium was assigned 100, and the activity in the absence of calcium was assigned 0. From the amount of a particular agent added into the reaction solution to produce an enzymatic activity depression of 50%, the agent was assigned an $IC_{50}$.

Result is shown in Table 2.

TABLE 2

| Test compound | $IC_{50}$ ($\mu M$) |
|---|---|
| Example 1 | 31 |

The following example is given by way of illustration only, and is not to be construed as limiting:

EXAMPLE 1

N-(2-Aminoethyl)-5-chloroisoquinoline-8-sulfonamide 2 hydrochloride (1) A solution of 5.00 g of 5-chloroisoquinoline in 8ml of chlorosulfonic acid was heated for 3 hours at 170° C. After cooling, the reaction mixture was poured into ice-water and extracted with chloroform. The chloroform layer was washed with water, dried and then added to a solution of 5.87 g of 2-(N-benzyloxycarbonylamino)ethylamine and 10 ml of triethylamine in 50 ml of methanol under ice-water cooling with stirring. The reaction mixture was stirred for 2 hours at room temperature and then filtered. The filtrate was concentrated and to the residue was added chloroform. The obtained precipitate was filtered off to give 2.50 g of N-(2-benzyloxycarbonylaminoethyl)-5-chloroisoquinoline-8-sulfonamide as colorless crystals.

(2) A solution of 3.80 g of N-(2-benzyloxycarbonylaminoethyl)-5-chloroisoquinoline-8-sulfonamide in 5 ml of 25% hydrogen bromide acetic acid solution was stirred for 3 hours at room temperature. Ether was added to the reaction mixture and the obtained precipitate was filtered. The precipitate was dissolved in water and the solution was made alkaline with potassium carbonate. The obtained precipitate was filtered off to give 1.30 g of pale brown crystals. The free base was converted into the hydrochloride in a usual manner, using gaseous hydrogen chloride in a solvent comprising ethanol, and the resulting salt was recrystallized from a mixture of ethanol and ether to give pale yellow prisms, m.p. 177°–180° C.

High resolution MS: $C_{11}H_{12}ClN_3O_2S$
Calculated m/z: 285.0339, 287.0309.
Found m/z: 285.0359, 287.0334.

EXAMPLE 2

N-(2-Aminoethyl)isoquinoline-8-sulfonamide 2 hydrochloride

A solution of 1.40 g of N-(2-aminoethyl)-5-chloroisoquinoline-8-sulfonamide 2 hydrochloride in 100 ml of methanol and 20 ml of aqueous ammonia solution was hydrogenated for 6 hours over 0.1 g of palladium-carbon at atmospheric pressure at room temperature. The catalyst was removed by filtration and the filtrate was concentrated. The residue was dissolved in methanol and filtered. The filtrate was concentrated to give 1.20 g of pale brown crystals. The free base was converted into the hydrochloride in a usual manner, using gaseous hydrogen chloride in a solvent comprising ethanol, and the resulting salt was recrystallized from a mixture of methanol and isopropanol to give pale brown prisms, m.p.200°–202° C.

High resolution MS: $C_{11}H_{13}N_3O_2S$
Calculated m/z: 251.0729.
Found m/z: 251.0733.

| Example 3: Tablet formulation | |
| --- | --- |
| Compound of Example 1 | 1.0 mg |
| lactose | 94.0 mg |
| corn starch | 34.0 mg |
| crystal cellulose | 20.0 mg |
| magnesium stearate | 1.0 mg |
| | 150.0 mg |

| Example 4: Capsule formulation | |
| --- | --- |
| Compound of Example 1 | 2.0 mg |
| lactose | 70.0 mg |
| corn starch | 27.0 mg |
| magnesium stearate | 1.0 mg |
| capsule | |
| | 100.0 mg |

| Example 5: Granule formulation | |
| --- | --- |
| Compound of Example 1 | 2.0 mg |
| D-mannitol | 446.0 mg |
| lactose | 420.0 mg |
| crystal cellulose | 100.0 mg |
| hydroxypropylcellulose | 32.0 mg |
| | 1000.0 mg |

| Example 6: Powder formulation | |
| --- | --- |
| Compound of Example 1 | 2.0 mg |
| lactose | 993.0 mg |
| hydroxypropylmethylcellulose | 5.0 mg |
| | 1000.0 mg |

| Example 7: Injection formulation | |
| --- | --- |
| Compound of Example 1 | 1.0 mg |
| sodium chloride | 18.0 mg |
| hydrochloric acid | |
| distilled water for injection | a proper quantity 2 ml |

| Example 8: Suppository formulation | |
| --- | --- |
| Compound of Example 1 | 1.0 mg |
| hard fat (Witepsol)(TM) | 1499.0 mg |
| | 1500.0 mg |

In conclusion, from the foregoing, it is apparent that the present invention provides novel isoquinolinesulfonamides, which are useful in the alleviation of circulatory disorders and as biochemical tools, and pharmaceutical compositions thereof, as well as a novel method of treating therewith, all having the foregoing enumerated characteristics and advantages.

It is to be understood that the invention is not to be limited to the exact details of operation or to the exact compounds, compositions, methods, procedures, or embodiments shown and described, as modifications and equivalents will be apparent to one skilled in the art, and the invention is therefore to be limited only be the full scope which can be legally accorded to the appended claims.

What is claimed is:

1. An isoquinolinesulfonamide selected from: the compound N-(2-aminoethyl)-5-chloroisoquinoline-8-sulfonamide and pharmacologically-acceptable acid addition salts thereof.

2. A compound of claim 1 which is N-(2-Aminoethyl)-5-chloroisoquinoline-8-sulfonamide 2 hydrochloride.

3. A pharmaceutical composition suitable for use in the treatment of circulatory disorders, comprising an effective amount of a compound of claim 1, together with a compatible pharmaceutically-acceptable carrier or coating.

4. A method for the treatment of a subject afflicted with a circulatory ailment, comprising the step of administering to the said subject an amount of a compound of claim 1 which is effective for alleviation of said ailment.

* * * * *

UNITED STATES PATENT AND TRADEMARK OFFICE
CERTIFICATE OF CORRECTION

PATENT NO. : 4,943,581

DATED : July 24, 1990

INVENTOR(S) : Hiroyoshi Hidaka, Toshio Tanaka, Yasuo Itoh, Hideo Kato, Eiichi Koshinaka, Kazuya Mitani, Shunichiro Sakurai It is certified that error appears in the above-identified patent and that said Letters Patent is hereby corrected as shown below:

Column 2, line 65; "solve to which" should read -- solvent which --.

Column 6, line 49; "be" second occurrence; should read -- by --.

Signed and Sealed this

Twenty-ninth Day of October, 1991

Attest:

HARRY F. MANBECK, JR.

*Attesting Officer*     *Commissioner of Patents and Trademarks*